(12) United States Patent
Battiato et al.

(10) Patent No.: US 8,459,200 B2
(45) Date of Patent: Jun. 11, 2013

(54) EXPOSURE INDICATING DEVICE

(75) Inventors: James M. Battiato, St Paul, MN (US); Dora M. Paolucci, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 342 days.

(21) Appl. No.: 12/997,650

(22) PCT Filed: Jun. 15, 2009

(86) PCT No.: PCT/US2009/047360
§ 371 (c)(1),
(2), (4) Date: Dec. 13, 2010

(87) PCT Pub. No.: WO2010/002575
PCT Pub. Date: Jan. 7, 2010

(65) Prior Publication Data
US 2011/0088611 A1 Apr. 21, 2011

Related U.S. Application Data

(60) Provisional application No. 61/076,839, filed on Jun. 30, 2008.

(51) Int. Cl.
*A62B 18/08* (2006.01)
*G01N 21/27* (2006.01)
*G01N 21/29* (2006.01)

(52) U.S. Cl.
USPC .................... 116/206; 96/117.5; 55/DIG. 34; 422/119

(58) Field of Classification Search
USPC .............. 116/206; 422/88, 91, 119; 436/902; 96/117.5; 55/DIG. 33, DIG. 34; 128/202.22
See application file for complete search history.

(56) References Cited

U.S. PATENT DOCUMENTS

| 1,537,519 | A | 5/1925 | Yablick |
| 3,966,440 | A | 6/1976 | Roberts |
| 4,146,887 | A | 3/1979 | Magnante |
| 4,154,586 | A | 5/1979 | Jones et al. |
| 4,155,358 | A | 5/1979 | McAllister et al. |
| 4,326,514 | A | 4/1982 | Eian |
| 4,421,719 | A | 12/1983 | Burleigh |

(Continued)

FOREIGN PATENT DOCUMENTS

| WO | WO 96/12523 A1 | 5/1996 |
| WO | WO 00/54840 A1 | 9/2000 |

(Continued)

OTHER PUBLICATIONS

Kresge, C.T., et al.; "Ordered mesoporous molecular sieves synthesized by a liquid-crystal template mechanism", *Nature* (Oct. 22, 1992); vol. 359; pp. 710-712.

(Continued)

*Primary Examiner* — R. A. Smith
(74) *Attorney, Agent, or Firm* — Gregg H. Rosenblatt

(57) ABSTRACT

An exposure indicating device disposed in a respirator system. The exposure indicating device comprises a diffractive optical element. The exposure indicating device comprises a material having an index of refraction that changes as a function of exposure to a chemical vapor, where the exposure indicating device provides an optical signal that changes in optical property as a function of exposure to the chemical vapor.

15 Claims, 5 Drawing Sheets

U.S. PATENT DOCUMENTS

| | | | |
|---|---|---|---|
| 4,530,706 | A | 7/1985 | Jones |
| 4,597,942 | A | 7/1986 | Meathrel |
| 4,684,380 | A | 8/1987 | Leichnitz |
| 4,847,594 | A | 7/1989 | Stetter |
| 5,297,544 | A | 3/1994 | May et al. |
| 5,323,774 | A | 6/1994 | Fehlauer |
| 5,376,554 | A | 12/1994 | Vo-Dinh |
| H1470 | H | 8/1995 | Ewing et al. |
| 5,512,882 | A | 4/1996 | Stetter et al. |
| 5,611,998 | A | 3/1997 | Aussenegg et al. |
| 5,659,296 | A | 8/1997 | Debe et al. |
| 5,666,949 | A | 9/1997 | Debe et al. |
| 5,783,836 | A | 7/1998 | Liu et al. |
| 5,858,457 | A | 1/1999 | Brinker et al. |
| 6,007,904 | A | 12/1999 | Schwotzer et al. |
| 6,130,748 | A | 10/2000 | Krüger et al. |
| 6,248,539 | B1 | 6/2001 | Ghadiri et al. |
| 6,312,793 | B1 | 11/2001 | Grill et al. |
| 6,375,725 | B1 | 4/2002 | Bernard et al. |
| 6,497,756 | B1 | 12/2002 | Curado et al. |
| 6,573,305 | B1 | 6/2003 | Thunhorst et al. |
| 6,701,864 | B2 | 3/2004 | Watson, Jr. et al. |
| 8,182,748 | B2 * | 5/2012 | Voipio et al. ............... 422/82.05 |
| 2004/0135684 | A1 | 7/2004 | Steinthal et al. |
| 2004/0184948 | A1 | 9/2004 | Rakow et al. |
| 2004/0189982 | A1 | 9/2004 | Galarneau et al. |
| 2004/0223876 | A1 | 11/2004 | Kirollos et al. |
| 2005/0188749 | A1 | 9/2005 | Custer et al. |
| 2007/0141580 | A1 | 6/2007 | David et al. |
| 2008/0002302 | A1 | 1/2008 | Kwon et al. |
| 2008/0063575 | A1 * | 3/2008 | Rakow et al. ................ 422/119 |
| 2008/0063873 | A1 | 3/2008 | Stapleton et al. |
| 2008/0063874 | A1 | 3/2008 | Rakow et al. |
| 2008/0160858 | A1 | 7/2008 | Paolucci et al. |

FOREIGN PATENT DOCUMENTS

| | | |
|---|---|---|
| WO | WO 2004/057314 A2 | 7/2004 |
| WO | WO 2005/012397 A2 | 2/2005 |
| WO | WO 2009153406 A1 * | 12/2009 |

OTHER PUBLICATIONS

Ogawa, Makoto; "A simple sol-gel route for the preparation of silica-surfactant mesostructured materials", *Chemical Communications* (1996); pp. 1149-1150.

Wei, Y. et al.; "A Non-surfactant Templating Route to Mesoporous Silica Materials", *Advanced Materials* (Mar. 1998); vol. 10, No. 4; pp. 313-316.

Goddard, N. J., et al.; "Resonant grating sensors using frustrated total-internal reflection", *Sensors and Actuators B* (1998); vol. 51; pp. 131-136.

Butler, T.M., et al.; "Integrated optical Bragg-grating-based chemical sensor on a curved input edge waveguide structure", *Optics Letters* (Apr. 15, 1999); vol. 24, No. 8; pp. 525-527.

Walheim, S., et al.; "Nanophase-Separated Polymer Films as High-Performance Antireflection Coatings", *Science* (1999); vol. 283; pp. 520-522.

Challener, W.A., et al.; "A multilayer grating-based evanescent wave sensing technique", *Sensors and Actuators B* (2000); vol. 71; pp. 42-46.

Krause, B., et al.; "Bicontinuous Nanoporous Polymers by Carbon Dioxide Foaming", *Macromolecules* (2001); vol. 34; pp. 8792-8801.

Dmitruk, N. L., et al.; "Characterization and application of multilayer diffraction gratings as optochemical sensors", *Sensors and Actuators A* (2001); vol. 88; pp. 52-57.

Bailey, R.C. & Hupp, J.T.; "Large-Scale Resonance Amplification of Optical Sensing of Volatile Compounds with Chemoresponsive Visible-Region Diffraction Gratings", *Journal American Chemical Society* (2002); vol. 124, No. 23; pp. 6767-6774.

Bailey, R.C. & Hupp, J.T.; "Micropatterned Polymeric Gratings as Chemoresponsive Volatile Organic Compound Sensors: Implications for Analyte Detection and Identification via Diffraction-Based Sensor Arrays", *Analytical Chemistry* (May 15, 2003); vol. 75, No. 10; pp. 2392-2398.

Budd, P.M., et al.; "Polymers of intrinsic microporosity (PIMs): robust, solution-processable, organic nanoporous materials", *Chemical Communications* (2004); pp. 230-231.

Jia, J., et al.; "Synthesis of Microporous Silica Templated by Gelatin", *Chemistry Letters* (2004); vol. 33, No. 2; pp. 202-203.

McKeown, N. B., et al.; "Polymers of Intrinsic Microporosity (PIMs): Bridging the Void between Microporous and Polymeric Materials", *Chemistry: A European Journal* (2005); vol. 11; pp. 2610-2620.

Budd, P.M., et al.; "Free volume and intrinsic microporosity in polymers", *Journal of Materials Chemistry* (2005); vol. 15; pp. 1977-1986.

Hsiao, et al.; "Organic Solvent Vapor Detection Using Holographic Photopolymer Reflection Gratings", *Advanced Materials* (2005); vol. 17; pp. 2211-2214.

* cited by examiner

EXPOSURE INDICATING DEVICE

CROSS REFERENCE TO RELATED APPLICATIONS

This application is a national stage filing under 35 U.S.C. 371 of PCT/US2009/047360, filed Jun. 15, 2009, which claims priority to U.S. Provisional Application No. 61/076,839, filed Jun. 30, 2008, the disclosure of which is incorporated by reference in its/their entirety herein.

BACKGROUND

1. Field

The present invention is directed to an exposure indicating device.

2. Related Art

A variety of respirator systems exist to protect users from exposure to dangerous chemicals. Examples of these systems include negative pressure or powered air respirators which use a cartridge containing a sorbent material for removing harmful substances from the ambient air, and supplied air respirators.

A number of protocols have been developed to evaluate the air being delivered to the user. These protocols may also be used to determine whether the sorbent material is near depletion. The protocols include sensory warning, administrative control, passive indicators, and active indicators.

For example, an end-of-life sensor ("EOLS") or end-of-service-life indicator ("ESLI") can warn that a filter element in such a device may be approaching saturation or may be ineffective against a particular material. Patents and applications relating to personal protection or respiratory protection (and in some instances to sensors or indicators in general or to EOLSs or ESLIs in particular) include U.S. Pat. No. 1,537,519 (Yablick), U.S. Pat. No. 3,966,440 (Roberts), U.S. Pat. No. 4,146,887 (Magnante), U.S. Pat. No. 4,154,586 (Jones et al.), U.S. Pat. No. 4,155,358 (McAllister et al.), U.S. Pat. No. 4,326,514 (Eian), U.S. Pat. No. 4,421,719 (Burleigh), U.S. Pat. No. 4,530,706 (Jones), U.S. Pat. No. 4,597,942 (Meathrel), U.S. Pat. No. 4,684,380 (Leichnitz), U.S. Pat. No. 4,847,594 (Stetter), U.S. Pat. No. 5,297,544 (May et al.), U.S. Pat. No. 5,323,774 (Fehlauer), U.S. Pat. No. 5,376,554 (Vo-Dinh), U.S. Pat. No. 5,512,882 (Stetter et al.), U.S. Pat. No. 5,666,949 (Debe et al. '949), U.S. Pat. No. 5,659,296 (Debe et al. '296), U.S. Pat. No. 6,375,725 B1 (Bernard et al.), U.S. Pat. No. 6,497,756 B1 (Curado et al.) and U.S. Pat. No. 6,701,864 B2 (Watson, Jr. et al.); US. Patent Application Publication Nos. US 2004/0135684 A1 (Steinthal et al.), US 2004/0189982 A1 (Galarneau et al.) US 2004/0223876 A1 (Kirollos et al.) and US 2005/0188749 A1 (Custer et al.); and PCT Published Patent Application No. WO 2004/057314 A2.

Other patents and patent applications relating to sensors or indicators but not to EOLSs or ESLIs include U.S. Pat. No. 5,611,998 (Aussenegg et al.), U.S. Pat. No. 5,783,836 (Liu et al.), U.S. Pat. No. 6,007,904 (Schwotzer et al.), U.S. Pat. No. 6,130,748 (Krüger et al.) and U.S. Pat. No. 6,248,539 (Ghadiri et al.); U.S. Patent Application Publication No. US 2004/0184948 A1 (Rakow et al.); and US Statutory Invention Registration No. H1470 (Ewing et al.).

SUMMARY

According to a first aspect of the present invention, an exposure indicating device is disposed in a respirator system. The exposure indicating device comprises a diffractive optical element. The exposure indicating device comprises a material having an index of refraction that changes as a function of exposure to a chemical vapor. The exposure indicating device provides an optical signal that changes in optical property as a function of exposure to the vapor. In a one aspect, the diffractive optical element comprises a diffraction grating.

In another aspect, the material comprises a nano-porous material having an index of refraction that changes as a function of exposure to the chemical vapor. In another aspect, the nano-porous material comprises an amorphous random covalent network that includes silicon, carbon, hydrogen and oxygen with a mean pore size in a range from about 0.5 to about 10 nanometers.

In another aspect, the diffractive optical element is formed from the nano-porous material.

In an alternative aspect, the diffractive optical element is substantially embedded in the nano-porous material. The diffractive optical element comprises a diffraction grating having an index of refraction that is substantially equal to an index of refraction of the surrounding nano-porous material prior to exposure to the chemical vapor. Also, the diffraction grating has an index of refraction that is different from an index of refraction of the surrounding nano-porous material prior to after sufficient exposure to the chemical vapor.

In one aspect, the device is a passive device. In another aspect, the device is an active device.

In one aspect, the diffractive optical element comprises a patterned microporous amorphous carbon material.

According to another aspect of the present invention, an exposure indicating device disposed in a respirator system includes a face mask having mounted thereon at least one replaceable air purifying respirator cartridge comprising a sorbent material. The exposure indicating device includes a diffractive optical element formed on a substrate, the substrate mounted to an inner sidewall of the at least one respirator cartridge. The mounting location on the sidewall of the at least one respirator cartridge is substantially transparent. The exposure indicating device comprises a nano-porous material having an index of refraction that changes as a function of exposure to a chemical vapor, where the exposure indicating device provides an optical signal that changes in optical property as a function of exposure to the chemical vapor.

In one aspect, the diffractive optical element is formed from the nano-porous material having an index of refraction that changes as a function of exposure to the chemical vapor.

In another aspect, the diffractive optical element is substantially embedded in the nano-porous material, where the nano-porous material is substantially surrounded by the sorbent material.

In another aspect, the diffractive optical element comprises a diffraction grating having an index of refraction that is substantially equal to an index of refraction of the surrounding nano-porous material prior to exposure to the chemical vapor and that is different from an index of refraction of the surrounding nano-porous material after sufficient exposure to the vapor. In one aspect, the exposure indicating device is a passive device.

The above summary of the present invention is not intended to describe each illustrated embodiment or every implementation of the present invention. The figures and the detailed description that follows more particularly exemplify these embodiments.

BRIEF DESCRIPTION OF THE DRAWINGS

The present invention will be further described with reference to the accompanying drawings, wherein.

Figure 1:
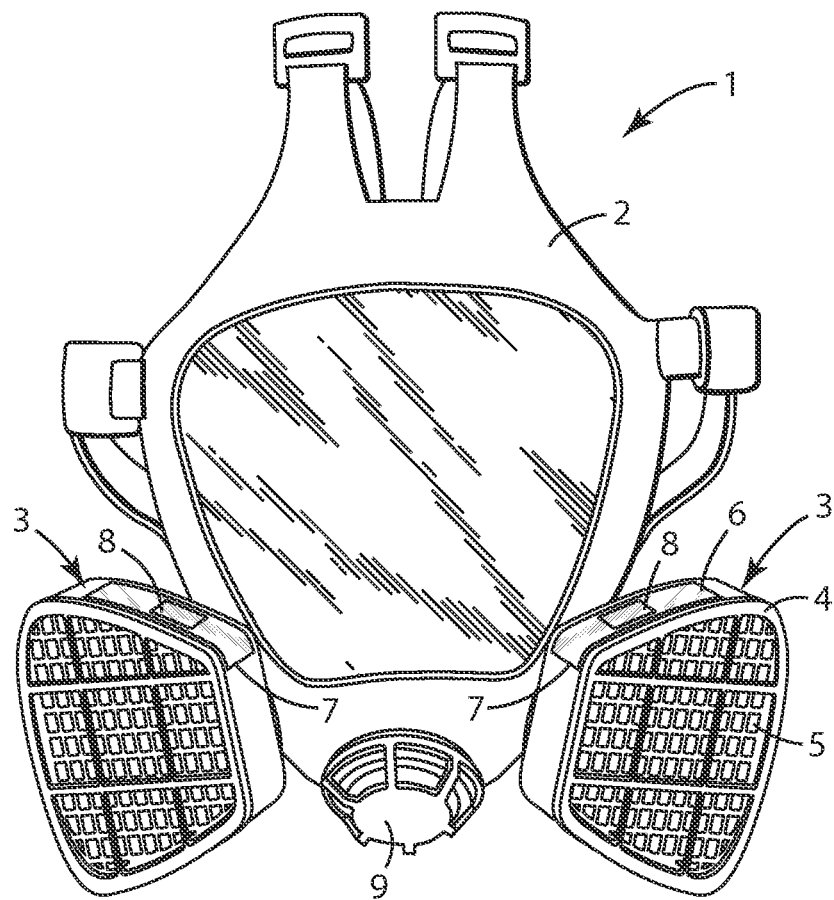
FIG. 1 is a schematic view of a respirator having an exposure indicating device according to an aspect of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF THE EMBODIMENTS

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "forward," "trailing," etc., may be used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention.

The present invention is directed to an exposure indicating device. In one aspect, the exposure indicating device is utilized with a personal respirator to indicate to the wearer that the purifying cartridges used with the respirator need to be replaced. In a preferred aspect, the exposure indicating device is an optically-based, passive device that changes its index of refraction as a function of exposure to a deleterious vapor or other airborne substance. Further, the exposure indicating device utilizes a diffractive optical element, such as a diffraction grating, to provide a visual indication that the purifying cartridge is near depletion. In one aspect, the diffractive element can be a nano-porous material. In another aspect, the diffractive element can be embedded in a nano-porous material.

Referring to FIG. 1, an exemplary personal respirator 1 includes a face mask 2 on which is mounted a pair of replaceable air purifying respirator cartridges 3. The cartridges 3 each serve as enclosures for a sorbent material (e.g., activated carbon and/or others described below) not shown in FIG. 1. The front cover 4 of each cartridge 3 includes a plurality of openings 5 that serve as gas inlets, permitting ambient air from the external environment to flow into cartridge 3, through the sorbent material and then through a passage (not labeled in FIG. 1) that serves as a gas outlet from cartridge 3 and an inlet to face mask 2. The sidewall 6 in each cartridge 3 is transparent or at least includes a transparent portion 7 through which a wearer of face mask 2 can see the exposure indicating device 8 (also referred to herein as an indicator 8 or an indicator 8'). In a preferred aspect, at least a substantial portion of sidewall 6 is transparent. The exposure indicating device 8 can be located near an upper surface of the sidewall 6 for more straightforward viewing by the wearer.

As described in more detail below, exposure indicating device 8 is optically responsive, undergoing a visibly discernible colorimetric change when the sorbent material becomes equilibrated with a particular vapor or target species (referred to herein simply as the vapor) at the conditions of exposure, thus aiding the wearer in recognizing that it is time to replace the cartridge or cartridges 3. Exhaled air exits respirator 1 through exhalation valve 9. The indicator may be used in a variety of respiratory protective devices. For example, the indicator may also be deployed in a single cartridge respirator or a powered air-purifying respirator.

Figure 2:
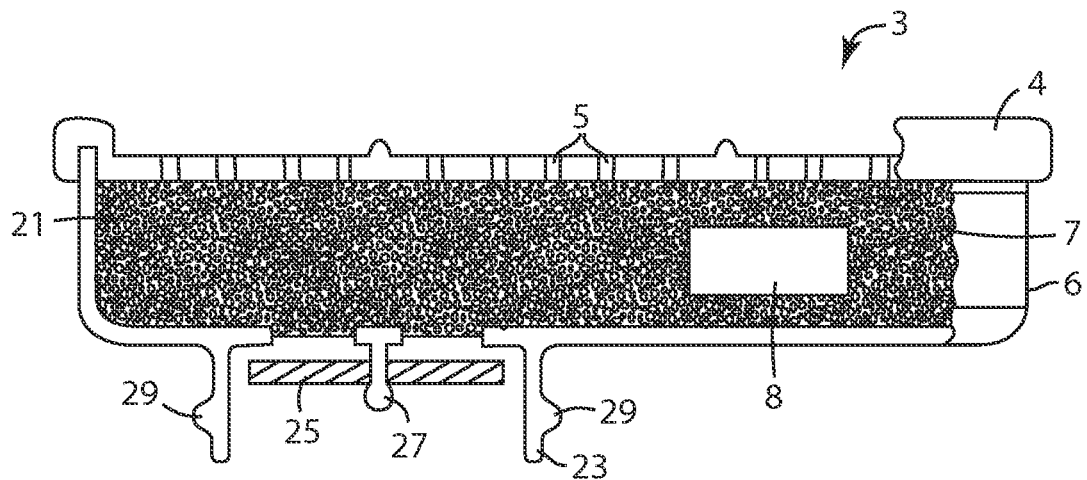
FIG. 2 is a section view of a respirator cartridge having an exposure indicating device according to an aspect of the invention.

FIG. 2 is a side view, partially in section, of respirator cartridge 3. If desired, the openings 5 could be sealed until use using for example a removable cover (not shown in FIG. 1 and FIG. 2) that would be removed before use. A bed of sorbent material 21 disposed within the cartridge absorbs or adsorbs vapors of interest passing from the openings 5 to outlet 23. A one-way inhalation valve can also be utilized. The one-way inhalation valve can be mounted on the main face piece of the respirator, or optionally, a one-way inhalation valve 25 can be mounted on a post 27 to prevent exhaled air from entering cartridge 3. A threaded or preferably bayoneted connector or connectors 29 can be used to removably couple cartridge 3 to mask 2. Sidewall 6 is either entirely transparent or it at least includes a substantially transparent portion 7. The transparent sidewall permits ambient light to pass into exposure indicating device 8.

The cartridges 3 would be removed and replaced with fresh cartridges 3 when a visibly discernible change in the appearance of exposure indicating device 8 indicates that the sorbent material 21 underneath exposure indicating device 8 has become equilibrated with the vapor at the conditions of exposure. In a preferred aspect, as explained in further detail below, the exposure indicating device 8 can provide a bright rainbow-type, multi-color appearance upon vapor equilibrium. Alternatively, such a change in appearance may include a change in color such as from green to red or other color.

In a further alternative, by configuring exposure indicating device 8 so that it covers the full length of the vapor flow path, an appearance change (e.g., a color change) would advance with the flow of vapor through the sorbent material 21 and past exposure indicating device 8. The advancing appearance change would indicate the remaining service life for cartridge 3 (like a bar gauge or fuel gauge) rather than just the end of service life, especially where appropriate care is taken to design cartridge 3 so that its remaining lifetime is linearly proportional to the spatial vapor front penetration past exposure indicating device 8.

Alternatively, exposure indicating device 8 could be placed toward the end of the flow path only so as to give warning only at the desired remaining service life percentage. Exposure indicating device 8 may if desired include a pattern or reference color to assist in visual discernment of changes in the appearance of exposure indicating device 8.

As mentioned, appearance changes in exposure indicating device 8 could be visibly monitored under ambient lighting, thereby providing EOLS or ESLI as a passive device. Alternatively, indicator 8 could be illuminated using an external light source such as a light emitting diode (LED) and evaluated using a photodetector mounted on the periphery of cartridge 3 to provide an optoelectronic signal. In addition, light could be delivered to the exposure indicating device 8 via one or more optical fibers. Whether viewed under ambient light or by using an external light source and photodetector, the breadth of chemical detection could if desired be increased in a variety of ways. For example, a small array of indicators traversing the vapor flow path could be employed.

Figure 3A:
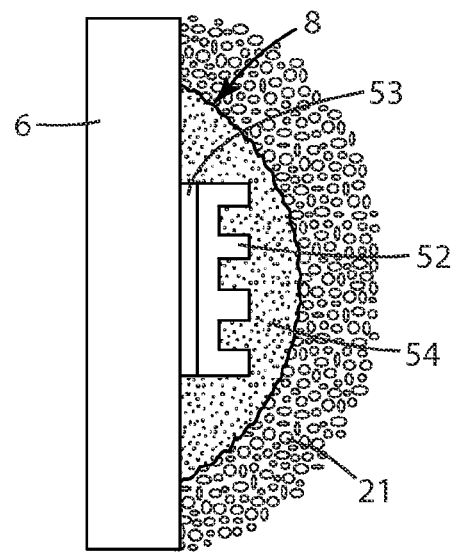
FIG. 3A is a schematic view of an exposure indicating according to an aspect of the invention.
Figure 3B:
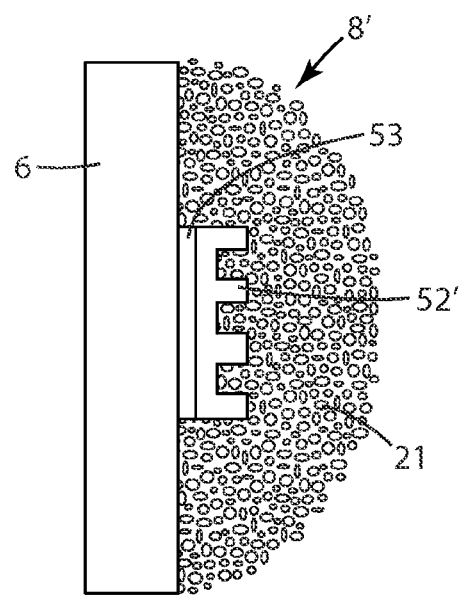
FIG. 3B is a schematic view of an exposure indicating device according to another aspect of the invention.

FIGS. 3A and 3B show different embodiments of exemplary exposure indicating devices, namely indicator 8 (FIG. 3A) and indicator 8' (FIG. 3B).

FIG. 3A shows a schematic view of an exemplary indicator 8. In one embodiment, indicator 8 includes a diffractive element. In a preferred aspect, the diffractive element comprises a diffraction grating 52 disposed on a substrate 53. The formation of the grating 52 on substrate 53 is described in further detail below. Alternatively, the grating 52 can be etched into substrate 53.

The diffractive element, here diffraction grating 52, is embedded in a nano-porous material 54, which substantially surrounds the diffraction grating (i.e., not on all sides). The embedding may be accomplished by a conventional spray coat process, dip coat process, or similar method, where the nano-porous material could embed the solid grating and/or fill the "grooves" formed on the diffractive element. The substrate 53 is disposed on an inner surface of sidewall 6 and may be adhered to a surface of sidewall 6 by using a conventional adhesive, such as an epoxy. The sorbent material 21 envelops the embedded indicator 8 and substantially surrounds it.

According to an exemplary aspect of the present invention, the exposure indicating device experiences a change in refractive index as a function of exposure. In the particular embodiment of FIG. 3A, the grating 52 has a constant index of refraction ($n_g$) while the nano-porous material 54 has a variable index of refraction, where the index of refraction changes as a function of the material's exposure to a particular vapor. In operation, a nano-porous material 54 is selected having an initial index of refraction ($n_{pi}$) that is the same as the index of refraction of the exemplary diffraction grating (i.e., $n_{pi}=n_g$). However, as the sorbent material 21 is exposed to the vapor, its index of refraction ($n_{pe}$) changes, such that $n_{pe} \neq n_g$.

Figure 4A:
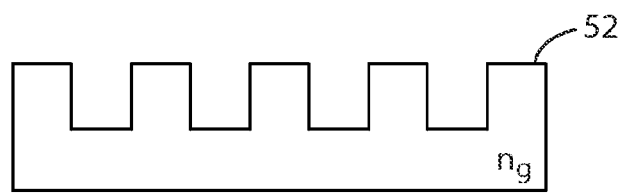
FIG. 4A is a schematic view of an exemplary grating.
Figure 4B:
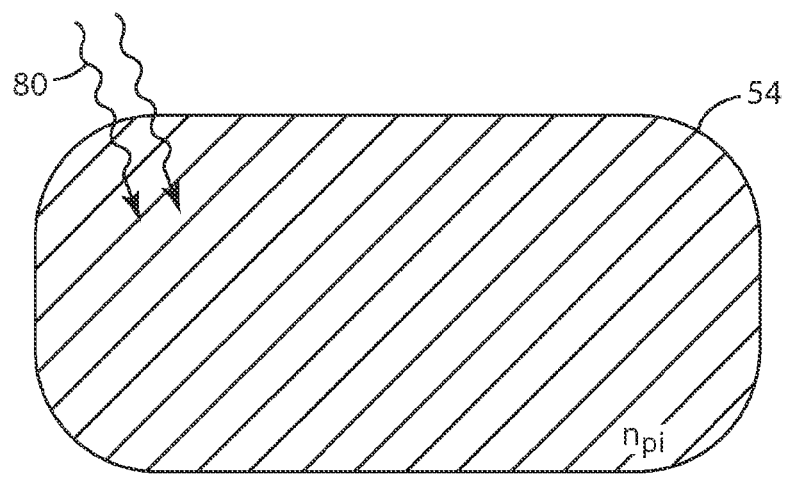
FIGS. 4B and 4C are schematic views of exposure indicating device before and after exposure according to an aspect of the invention.
Figure 4C:
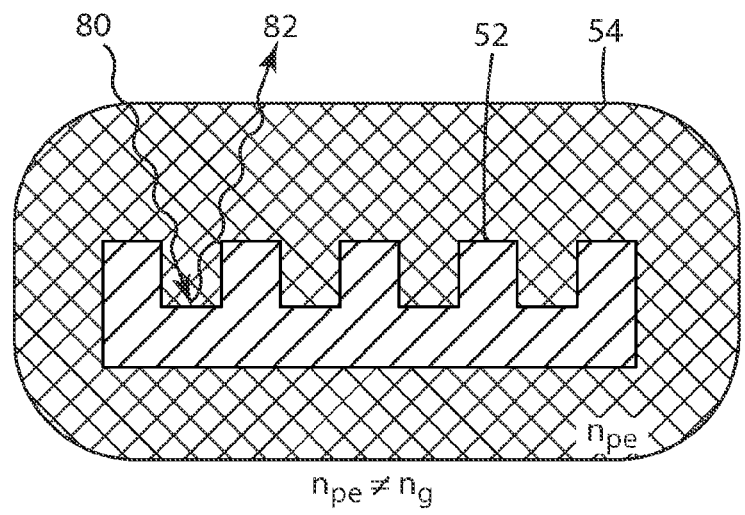

For example, as shown schematically in FIGS. 4A-4C, the appearance of the grating depends on the exposure level of the nano-porous material 54 to the vapor. In this embodiment, the diffractive element comprises a diffraction grating. As shown in FIG. 4A, diffraction grating 52 can be formed having a conventional structure of alternating peaks and valleys. Alternatively, the grating 52 may be formed as a blazed grating, a chirped grating, or other diffractive element, as would be apparent to one of ordinary skill in the art given the present description. The material used to form diffraction grating 52 has an initial index of refraction ($n_g$).

In operation, for this embodiment, the diffraction grating 52 is substantially surrounded by the nano-porous material 54. Thus, as shown in FIG. 4B, since nano-porous material 54 has an initial index of refraction ($n_{pi}$) that is the same as the index of refraction of the diffraction grating ($n_g$) (i.e. $n_{pi}=n_g$), light 80 passing into the nano-porous material 54 is unaffected by the presence of the embedded diffraction grating 52. However, as shown in FIG. 4C, as the nano-porous material 54 is exposed to the vapor, its index of refraction changes from ($n_{pi}$) to ($n_{pe}$), such that $n_{pe} \neq n_g$. As gratings are highly dispersive, a portion of the light 80 passing into the exposed nano-porous material 54 is diffracted by the embedded diffraction grating 52 (diffracted light 82) that is visible to a user as a diffraction pattern (e.g., a rainbow-type pattern). This diffraction pattern indicates to the user that the sorbent cartridge should be replaced.

In an alternative embodiment, the diffractive element can be replaced with a refractive element such as a lens. In this manner, the lens and the nano-porous material that surrounds it can have the same initial index of refraction. As the nano-porous material is exposed to the vapor, its index of refraction changes. Thus, the lens can bring into view a symbol or other structure that was not in view prior to the index change of the nano-porous material.

The nano-porous material 54 may comprise a homogeneous or heterogeneous material, and may, for example, be made from a mixture of inorganic components, a mixture of organic components, or a mixture of inorganic and organic components. The nano-porous material desirably has a range of pore sizes or a surface area selected to provide vapor sorption characteristics like those of the sorbent media. Suitable porosity can be obtained by using porous materials such as foams made from high internal phase emulsions, such as those described in U.S. Pat. No. 6,573,305 B1 (Thunhorst et al.). Porosity may also be obtained via carbon dioxide foaming to create a microporous material (see "Macromolecules", 2001, vol. 34, pp. 8792-8801), or by nanophase separation of polymer blends (see "Science", 1999, vol. 283, p. 520). In general, the pore diameters preferably are smaller than the peak wavelength of the desired indicator coloration. Nano-sized pores are preferred, e.g., with average pore sizes of about 0.5 to about 20 nm, 0.5 to about 10 nm, or 0.5 to about 5 nm.

Representative inorganic nano-porous materials include porous silica, metal oxides, metal nitrides, metal oxynitrides and other inorganic materials that experience a change in index of refraction through exposure to a particular vapor. For example, the inorganic nano-porous materials may be silicon oxides, silicon nitrides, silicon oxynitrides, aluminum oxides, titanium oxides, titanium nitride, titanium oxynitride, tin oxides, zirconium oxides, zeolites or combinations thereof. Porous silica is an exemplary nano-porous material.

Porous silicas may be prepared, for example, using a sol-gel processing route and made with or without an organic template. Exemplary organic templates include surfactants, e.g., anionic or nonionic surfactants such as alkyltrimethylammonium salts, poly(ethyleneoxide-co-propylene oxide) block copolymers and other surfactants or polymers that will be apparent to persons having ordinary skill in the art. The sol-gel mixture may be converted to a silicate and the organic template may be removed to leave a network of micropores within the silica.

Representative porous silica materials are described in Ogawa et al., *Chem. Commun.* Pp. 1149-1150 (1996), in Kresge et al., *Nature*, Vol. 359, pp. 710-712 (1992), in Jia et al., *Chemistry Letters*, Vol. 33(2), pp. 202-203 (2004) and in U.S. Pat. No. 5,858,457 (Brinker et al.). A variety of organic molecules may also be employed as organic templates. For example, sugars such as glucose and mannose may be used as organic templates to generate porous silicates, see Wei et al, *Adv. Mater.* 1998, Vol. 10, p. 313 (1998). Organo-substituted siloxanes or organo-bis-siloxanes may be included in the sol-gel composition to render the micropores more hydrophobic and limit sorption of water vapor. Plasma chemical vapor deposition may also be employed to generate porous inorganic materials. Examples of such materials are described in U.S. Pat. No. 6,312,793 (Grill et al.) and U.S. Publication No. 20070141580. For example, U.S. Publication No. 20070141580 describes an amorphous random covalent network that includes silicon, carbon, hydrogen and oxygen with a mean pore size in a range from 0.5 to 10 nanometers. Another example material comprises a silicon/carbon/oxygen plasma deposited film (SiCO) described in U.S. patent application Ser. No. 11/618,010.

Representative organic nano-porous materials include polymers, copolymers (including block copolymers) and mixtures thereof prepared or preparable from classes of monomers including hydrophobic acrylates and methacrylates, difunctional monomers, vinyl monomers, hydrocarbon monomers (olefins), silane monomers, fluorinated monomers, hydroxylated monomers, acrylamides, anhydrides, aldehyde-functionalized monomers, amine- or amine salt-functionalized monomers, acid-functionalized monomers, epoxide-functionalized monomers and mixtures or combinations thereof. U.S. Patent Application Publication No. US 2004/0184948 A1 contains an extensive list of such monomers and reference is made thereto for further details. The above-mentioned polymers having intrinsic microporosity (PIMs) provide particularly desirable materials. PIMs typically are non-network polymers that form microporous solids. Due to their typically highly rigid and contorted molecular structures, PIMs are unable to fill space efficiently, thus providing the disclosed microporous structure. Suitable PIMs include, but are not limited to, polymers disclosed in "Polymers of intrinsic microporosity (PIMs): robust, solution-processable, organic microporous materials," Budd et al., *Chem. Commun.*, 2004, pp. 230-231. Additional PIMs are disclosed in Budd et al., *J. Mater. Chem.*, 2005, 15, pp. 1977-1986, in McKeown et al., *Chem. Eur. J.* 2005, 11, No. 9, 2610-2620 and in Published PCT application No. WO 2005/012397 A2 (McKeown et al.).

One or more polymers within an organic layer may be at least partially crosslinked. Crosslinking may be desirable in some embodiments because it can increase mechanical stability and sensitivity to certain analytes. Crosslinking can be achieved by incorporating one or more multifunctional monomers into the layer, by subjecting the layer to, e.g., electron beam or gamma ray treatment, by adding or forming coordination compounds or ionic compounds in the layer, or by forming hydrogen bonds in the layer. In one exemplary embodiment, crosslinking is carried out in the presence of a porogen which may be subsequently extracted from the crosslinked system to yield a porous material. Suitable porogens include, but are not limited to, inert organic molecules, such as normal alkanes (e.g., decane) or aromatics (e.g., benzene or toluene). Other crosslinked polymers include the above-mentioned highly crosslinked styrenic polymers.

If desired, the nano-porous material may be treated to modify its surface properties or adsorption characteristics. A variety of such treatments may be employed, e.g., by exposing the micropores of an inorganic nano-porous material to a suitable organosilane compound.

For many applications, the nano-porous material is hydrophobic. This will reduce the chance that water vapor (or liquid water) will cause a change in the nano-porous material.

FIG. 3B shows a schematic view of an alternative exemplary indicator 8'. In a preferred aspect, indicator 8' includes a diffractive element, such as diffraction grating 52', disposed on a substrate 53. The formation of the grating 52' is described in further detail below. Alternatively, the grating 52' can be etched into substrate 53.

The diffractive element, here diffraction grating 52', comprises a nano-porous material whose refractive index changes as a function of exposure to a vapor, such that its index of refraction changes from an initial value ($n_{gi}$) to an exposed value ($n_{ge}$), such that $n_{ge} \neq n_{gi}$. The substrate 53 is disposed on an inner surface of sidewall 6 and may be adhered to a surface of sidewall 6 by using a conventional adhesive, such as an epoxy. The sorbent material 21 envelops the embedded indicator 8.

In one aspect, referring back to the embodiment of FIG. 3A, the diffractive element can be a diffraction grating 52 formed on a silica or otherwise transparent substrate. In this aspect, the index of refraction of the diffraction grating 52 remains constant while the index of refraction of the surrounding nano-porous material changes as a function of exposure.

In an alternative aspect, for the embodiment of FIG. 3B, diffraction grating 52' comprises a nano-porous material whose index of refraction changes as a function of exposure. The diffraction grating 52' may be manufactured as follows. In one exemplary aspect, the diffraction grating 52 is formed as a thin film stack of diamond-like carbon (DLC) and diamond-like glass (DLG). The deposition of DLC and DLG materials is described in U.S. patent application Ser. No. 11/618,010.

Figure 5A:
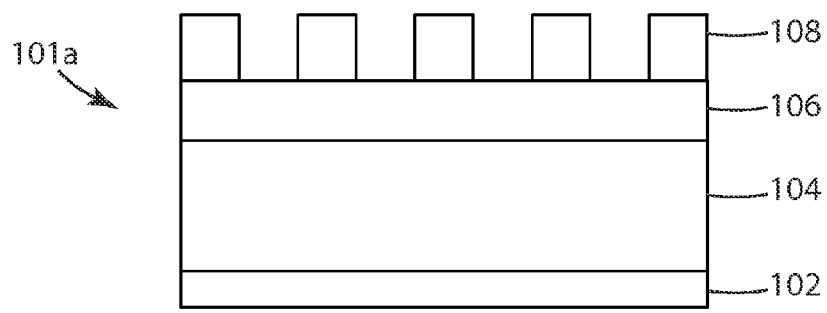
FIGS. 5A-5C are schematic views of a process for making a grating for an exposure indicating device according to another aspect of the invention.

FIG. 5A shows a schematic view of an in-process grating 101a that is used to form final grating 52'. The initial stack comprises a substrate 102, a DLC layer 104 formed on the substrate, a DLG layer 106 formed on the DLC layer, and a photoresist layer 108 formed on the DLG layer. In a preferred aspect, substrate 102 is a silica material. Colored glasses or other transparent substrate materials can also be utilized. Other gratings can formed on silicon based substrates, which are best utilized in an active system, incorporating a separate light source and/or optical fibers, such as is described above.

Deposition can be performed in a batch reactor, such as is available from Plasmatherm (e.g., model no. 3032). The substrate 102 can be primed before deposition of the DLC and DLG, e.g., using an oxygen plasma and a tetramethylsilane plasma. The thickness of the DLC 104 can be formed from about 500 nm to about 1000 nm (preferably about 800 nm) and the thickness of the DLG 106 can be formed from about 20 nm to about 100 nm (preferably about 50 nm). A conventional photoresist material, such as a positive photoresist material, having a thickness of about 500 nm, can be utilized (e.g., MICROPOSIT S1805, available from Rohm and Hass Electronic materials, Marlborough, Mass.). As shown in FIG. 5A, the photoresist 108 can have a standard alternating pattern. Alternatively, the photoresist 108 can have a suitable pattern for a blazed grating, a chirped grating, or other diffractive element. The patterning and development can be accomplished using conventional photolithographic techniques.

Figure 5B:
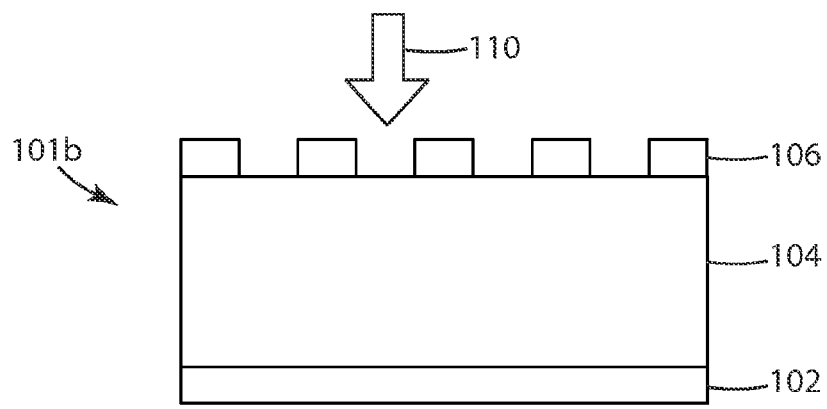
Figure 5C:
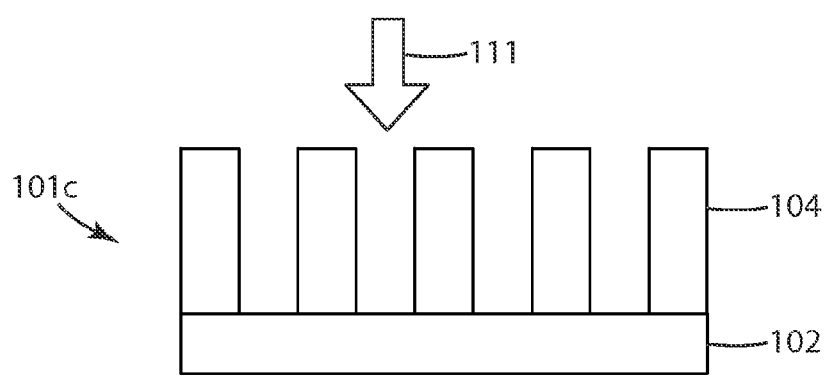

The photoresist pattern is then transferred to the DLG, as shown in the in-process structure 101b of FIG. 5B. For example, a reactive ion etching (RIE) technique can be employed to transfer the pattern. In one example, the DLG 106 can be etched using a C3F8/O2 etch. Of course, other etchants can also be utilized. This pattern is then further transferred to the DLC layer 104. For example, a conventional RIE technique, such as an O2 etch, can be utilized. The resultant in-process structure 101c is shown in FIG. 5C. After etching, the grating is annealed to result in a patterned microporous amorphous carbon material that changes index as a function of exposure to certain vapors.

In an experiment performed using a grating formed in accordance with the formation process of FIGS. 5A-5C, a grating was tested against a range of toluene challenged concentrations. A sample grating was placed in a test chamber. An evaporator was utilized to create toluene vapor that was injected into an air stream that was pumped (using an adjustable pump) into the test chamber. The sample grating was laid at an angle of about 45 degrees and illuminated with a conventional microscope lamp. A large core optical fiber was used to collect a portion of the reflected light signal. The reflected light comprised a rainbow type pattern. After exposure to 50 ppm of Toluene, the sample yielded a 17% increase in reflected signal at 775 nm. After exposure to 500 ppm of Toluene, the sample yielded a 25% increase in reflected signal at 775 nm.

Figure 6:
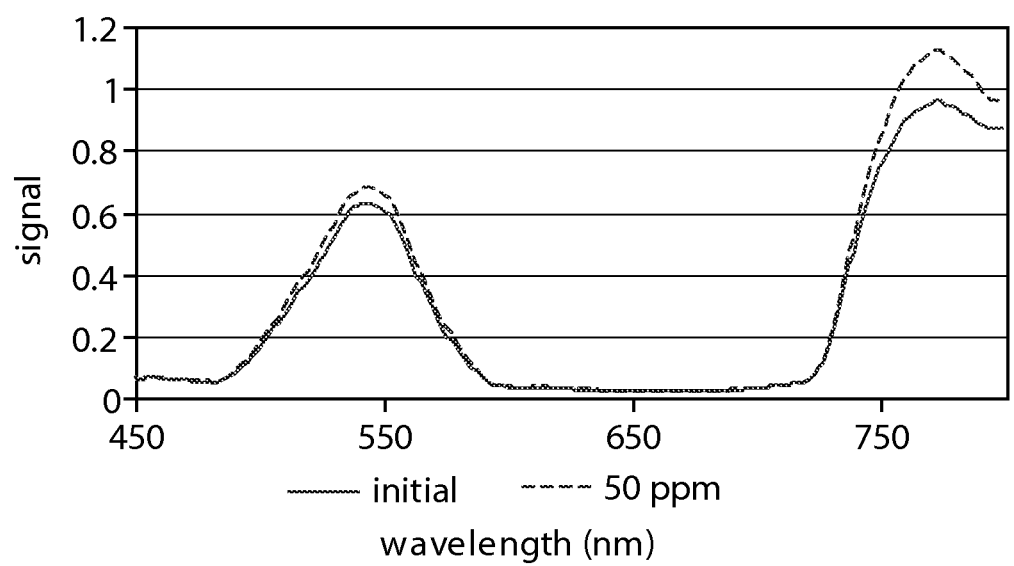
FIG. 6 is a graph showing the optical response of an example diffraction grating to changing exposure.

FIG. 6 provides a graph of the sample diffraction grating response to Toluene exposure for pre-exposure and 50 ppm exposure levels. The optical spectrum data of the sample was monitored with a tungsten halogen light source (R-LS-1, available from Ocean Optics), a reflection probe, and a USB-2000 spectrometer.

Accordingly, a nano-porous material in conjunction with a diffractive element, as part of an exposure indicating device for a respirator system, can be utilized for EOLS or ESLI applications.

Various modifications, equivalent processes, as well as numerous structures to which the present invention may be applicable will be readily apparent to those of skill in the art to which the present invention is directed upon review of the present specification.

We claim:

1. An exposure indicating device disposed in a respirator system, wherein the exposure indicating device comprises a diffractive optical element, wherein the exposure indicating device comprises a material having an index of refraction that changes as a function of exposure to a chemical vapor, wherein the exposure indicating device provides an optical signal that changes in optical property as a function of exposure to the chemical vapor.

2. The exposure indicating device of claim 1, wherein the material comprises a nano-porous material having an index of refraction that changes as a function of exposure to the chemical vapor.

3. The exposure indicating device of claim 2, wherein the diffractive optical element is formed from the nano-porous material.

4. The exposure indicating device of claim 3, wherein the diffraction grating comprises patterned microporous amorphous carbon material.

5. The exposure indicating device of claim 2, wherein the diffractive optical element is substantially embedded in the nano-porous material.

6. The exposure indicating device of claim 5, wherein the diffractive optical element comprises a diffraction grating having an index of refraction that is substantially equal to an index of refraction of the surrounding nano-porous material prior to exposure to the chemical vapor.

7. The exposure indicating device of claim 6, wherein the diffraction grating has an index of refraction that is different from an index of refraction of the surrounding nano-porous material prior to after sufficient exposure to the chemical vapor.

8. The exposure indicating device of claim 5, wherein the nano-porous material comprises an amorphous random covalent network that includes silicon, carbon, hydrogen and oxygen with a mean pore size in a range from about 0.5 to about 10 nanometers.

9. The exposure indicating device of claim 1, wherein the device is a passive device.

10. The exposure indicating device of claim 1, wherein the device is an active device.

11. An exposure indicating device disposed in a respirator system, the respirator system including a face mask having mounted thereon at least one replaceable air purifying respirator cartridge comprising a sorbent material, comprising:

a diffractive optical element formed on a substrate, the substrate mounted to an inner sidewall of the at least one respirator cartridge, wherein the mounting location on the sidewall of the at least one respirator cartridge is substantially transparent, wherein the exposure indicating device comprises a nano-porous material having an index of refraction that changes as a function of exposure to a chemical vapor, wherein the exposure indicating device provides an optical signal that changes in optical property as a function of exposure to the chemical vapor.

12. The exposure indicating device of claim 11, wherein the diffractive optical element is formed from the nano-porous material having an index of refraction that changes as a function of exposure to the chemical vapor.

13. The exposure indicating device of claim 11, wherein the diffractive optical element is substantially embedded in the nano-porous material, and wherein the nano-porous material is substantially surrounded by the sorbent material.

14. The exposure indicating device of claim 13, wherein the diffractive optical element comprises a diffraction grating having an index of refraction that is substantially equal to an index of refraction of the surrounding nano-porous material prior to exposure to the chemical vapor and that is different from an index of refraction of the surrounding nano-porous material after sufficient exposure to the vapor.

15. The exposure indicating device of claim 11, wherein the device is a passive device.

* * * * *